United States Patent [19]

Harfenist

[11] 4,329,365
[45] May 11, 1982

[54] FLUKICIDAL COMPOUNDS

[75] Inventor: Morton Harfenist, Chapel Hill, N.C.

[73] Assignee: Burroughs Wellcome Co., Research Triangle Park, N.C.

[21] Appl. No.: 43,490

[22] Filed: May 29, 1979

[30] Foreign Application Priority Data

May 30, 1978 [GB] United Kingdom ............... 24035/78

[51] Int. Cl.³ ...................... A01N 37/18; C07C 102/00
[52] U.S. Cl. ..................................... 424/324; 564/154; 564/221
[58] Field of Search .......................... 260/551 S, 513.7; 424/324, 303; 564/154, 223, 430, 221

[56] References Cited

U.S. PATENT DOCUMENTS

| | | | |
|---|---|---|---|
| 3,207,786 | 9/1965 | Yale et al. | 564/221 |
| 3,423,470 | 1/1969 | Rohr et al. | 260/556 B |
| 3,840,597 | 10/1974 | Moore et al. | 260/562 P |
| 4,090,865 | 5/1978 | Baker | 564/221 X |
| 4,166,858 | 9/1979 | Rowlands | 424/324 |
| 4,198,407 | 4/1980 | Rösner et al. | 424/249 |

FOREIGN PATENT DOCUMENTS

| | | |
|---|---|---|
| 2008065 | 1/1970 | France . |
| 2212149 | 7/1974 | France . |
| 2391203 | 12/1978 | France . |
| 935378 | 8/1963 | United Kingdom . |

OTHER PUBLICATIONS

Chem. Abstracts 81: 105514w.
Chem. Abstracts 92: 180816b.

Primary Examiner—Ethel G. Love
Attorney, Agent, or Firm—Donald Brown

[57] ABSTRACT

Diphenylethers of the formula:

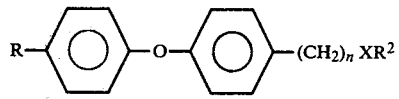

their synthesis, formulations containing them, methods of making such formulations, and their use in the treatment of liver fluke infections in mammals.

12 Claims, No Drawings

FLUKICIDAL COMPOUNDS

This invention relates to novel compounds, their preparation, formulations containing them, methods of making such formulations and to their use in the treatment of liver fluke infections in mammals.

Animals are infected with liver fluke when eating forage contaminated with encysted forms of cercariae, an intermediate stage in the life cycle of the fluke. The cercariae emerge from the cysts in the intestine of the host animal, penetrate the intestine wall, and make their way to the liver. At this stage they are microscopic in size, but grow as they wander around the liver parenchyma. This causes considerable destruction of the liver tissue and can give rise to the syndrome of acute fascioliasis which normally leads to the death of the host when massive infections are present. If the animal survives, the flukes eventually reach the bile ducts where they mature into adult worms. The presence of a massive infection in the bile ducts gives rise to the syndrome of chronic fascioliasis which is a serious debilitating disease of the host animal. In the past most liver fluke remedies have been known to kill only the adult and semiadult worms, and the immature worms have been resistant to attack by such remedies. However the compounds disclosed in U.K. Pat. No. 1,380,882 are effective in combatting infections of liver flukes in mammals, and are especially active in combatting infections of immature worms of Fasciola spp.

It has now been found by the Applicants that the novel compounds of formula (I) are effective in combatting infections of liver flukes in mammals.

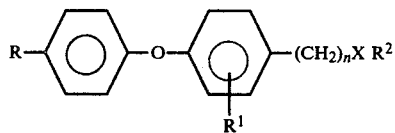
(I)

In formula (I):
R is selected from amino, monoalkanoylamino and dialkanoylamino, both of one to four carbon atoms;
$R^1$ is selected from hydrogen, alkyl of one to four carbon atoms, alkenyl of two to five carbon atoms and halo;
$R^2$ is selected from hydrogen and alkyl of one to four carbon atoms;
X is S, SO or $SO_2$; and
n is 0, 1, 2 or 3.

It will be appreciated by persons skilled in the art that acid addition salts may be formed of the compounds of formula (I). Unless the context indicates otherwise, wherever in the following reference is made to 'compounds of formula (I)' it should be understood that this term includes the acid addition salts of the compounds.

Compounds of formula (I) with particularly interesting anthelmintic properties are those wherein:
R is monoalkanoylamino of two or three carbon atoms;
$R^1$ is hydrogen;
$R^2$ is alkyl of one or two carbon atoms;
X is $SO_2$; and
n is 0 or 1.

The compounds of formula (I) may be prepared by standard methods well known in the art for the synthesis of compounds of analogous structure. Particular routes of synthesis which may be employed are dependent upon the chemical structure of the compound in question and will vary according to the reactive functional groups present in each compound.

The preparation of compounds of formula (I) wherein R is amino includes the reduction of a compound of formula (II):

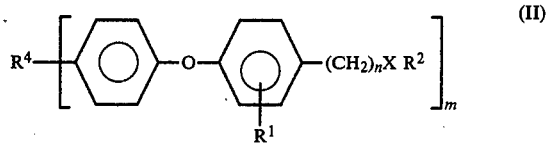
(II)

wherein $R^1$, $R^2$, n, and X are as defined previously, m is 1 or 2 and when m is 1, $R^4$ is nitro or nitroso; and when m is 2, $R^4$ is azo or azoxy.

The reduction may be conveniently effected by standard methods well-known in the art which include reaction with hydrogen in the presence of a metal or other hydrogen catalyst and a solvent such as aqueous acid, ethanol, or acetic acid; a metal and aqueous acid, for example, iron powder and dilute aqueous or ethanolic hydrochloric acid; and reducing agents such as stannous chloride in concentrated hydrochloric acid, ferrous hydroxide suspended in aqueous or ethanolic ammonia, iron powder in glacial acetic acid, aqueous dithionite, or other reagents known in the art to reduce nitro and nitroso compounds to amines.

Such reduction can be run in the presence of acylating agents (as described hereinbelow) to produce compounds of formula (I) wherein R is mono- or dialkanoylamino without isolation of the corresponding amine.

The preparation of compounds of formula (II) wherein $R^4$ is nitro or nitroso includes the reaction of a compound of formula (III):

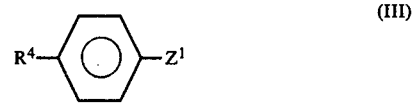
(III)

wherein $R^4$ is nitro or nitroso and $Z^1$ is a leaving group which may be selected from halo, nitro and alkane-, arene- or alkylarenesulphonyloxy with a compound of formula (IV):

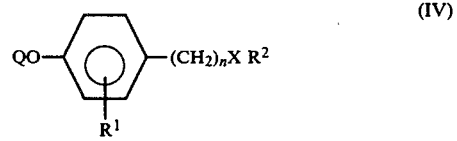
(IV)

wherein Q is an alkali metal atom, an alkaline earth metal atom or the ammonium radical and n, X, $R^1$ and $R^2$ are as defined in formula (I). The reaction may conveniently be effected by standard methods known in the art which include reaction in an appropriate polar inert solvent at an expedient temperature.

Compounds of formula (I) wherein R is amino may also be prepared by the deprotection of the corresponding protected amino compounds, for example acylated compounds of formula (I) wherein R is mono- or dialkanoylamino of 1 to 4 carbon atoms (or comparable arylamino compounds such as benzamides) and $R^1$, $R^2$, n and X are as previously defined. The reaction can be effected by acid hydrolysis, for example, by refluxing with aqueous hydrochloric acid, and water or ethanol, by alkaline hydrolysis e.g. with ethanolic or aqueous sodium hydroxide solution. Protection of the amino group as arylidine derivitives (Schiff bases) allows especially ready removal of the arylidine group to produce the amine by using aqueous acid.

Suitable methods for the preparation of compounds of formula (I) wherein R is monoalkanoylamino or dialkanoylamino include the acylation of a compound of formula (I) wherein R is amino and $R^1$, $R^2$, n and X are as previously defined. The acylation may be effected by standard methods which include reaction with the appropriate acid anhydride or acid halide in a suitable inert polar solvent at an expedient temperature.

Suitable methods for preparing the compounds of formula (1) wherein X is sulphoxide or sulphone, R is mono- or dialkanoylamino, and $R^2$ is alkyl of one to four carbon atoms include the oxidation of a compound of formula (V):

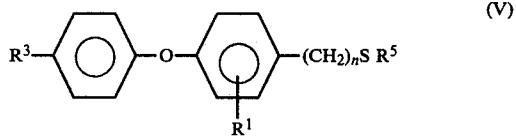

wherein $R^1$ and n are as defined previously, $R^5$ is alkyl of one to four carbon atoms and $R^3$ is mono- or dialkanoylamino. The oxidation may be carried out by standard techniques known in the art. Suitable oxidizing agents include hydrogen peroxide in acetic acid, peroxocarboxylic acids, alkali metal salts of the periodate ion, alkali metal salts of the permanganate ion and ozone. The reaction conditions will vary according to the reagent employed, the temperature utilized and the solvent used, but the correct choice will enable the oxidation to be proceeded with only in part or, if desired, completely, to yield the sulphoxide or the sulphone, respectively.

It is also possible to prepare the compounds of formula (I) wherein X is sulphone from the corresponding compounds wherein X is sulphoxide. Such methods would include those described above for oxidation of the corresponding sulphides.

The preparation of compounds of formula (I) wherein n is 1, 2 or 3, X is sulphide or sulphone, R is mono- or dialkanoylamino, and $R^2$ is alkyl of one to four carbon atoms, include the reaction of a compound of formula (VI):

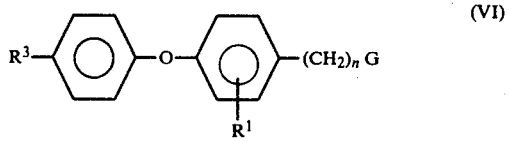

with a compound of formula (VII): $ZR^6$ wherein $R^1$ and $R^3$ are as defined previously, n is 1, 2 or 3, one of either G or Z is the sulphide or sulphonyl anion whilst the other is a standard leaving group as previously defined, and $R^6$ is an alkyl group of one to four carbon atoms. The reaction may conveniently be effected by standard methods known in the art in the presence of a suitable inert polar solvent at an expedient temperature.

A compound of formula (I) may be used in the treatment of liver fluke infections in mammals including *F. hepatica* in ruminants including sheep, cattle, goat and buffalo, and in the pig and horse, and *F. gigantica* in ruminants including sheep and cattle. The compound is preferably administered orally at a dose between 10 and 250 mg/kg; and preferably between 30 and 150 mg/kg.

A compound of formula (I) may be administered for the treatment of liver fluke infections as the raw chemical, but preferably as an ingredient of a pharmaceutical formulation which contains in addition one or more inert carrier materials commonly used in pharmaceutical formulations as a vehicle for the active ingredient. The amount of active ingredient present in such formulations may vary according to one or more of several factors but may comprise from 0.0001% to 95% by weight of the formulation. The preferred formulations are those suitable for oral administration, containing from 5 to 95% by weight of a compound of formula (I). If presented as the raw chemical, then a compound of formula (I) is preferably in the form of a powder.

In the context of the present invention, the qualification 'inert' means that the carrier is pharmaceutically acceptable to the host of the infection to which the formulation is administered.

The presentation of an active ingredient (namely, a compound of formula (I)) in a pharmaceutical formulation may be as discrete units, such as tablets, capsules or cachets, each containing a predetermined amount of the active ingredient; as a powder or granules; or as a solution or a suspension in an aqueous liquid, a nonaqueous liquid, or a water-in-oil liquid emulsion. The active ingredient may also be presented as a bolus, electuary or paste; in the feed or a feed supplement intended for the host animal; in pellets, salt licks or block licks which are especially suitable for large animals such as sheep and cattle.

The formulations may be made by any of the methods of pharmacy but all methods include the step of bringing into association by admixture the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulations. The formulations contain one or more of the usual accessory ingredients used to prepare anthelmintic formulations including: solid and liquid diluents (for example, lactose, sucrose, glucose, starches, dicalcium phosphate or calcium phosphate for tablets, granules, dispersible and wettable powders, cachets and capsules, arachis oil, olive oil, or ethyl oleate for soft capsules; water, or vegetable oil for aqueous and non-aqueous suspensions, emulsions, and pastes); binders (for example, starch, sugar, glucose, methyl cellulose, gum acacia, Irish mosse or gelatin for granules and tablets); surface active agents (for example sodium lauryl sulphate, cetrimide or polyoxyethylene sorbitan monolaureate for tablets, powders and granules; sodium salt of an alkyl naphthalene sulphonic acid, sorbitan monooleate, ceto-stearyl alcohol and an emulsifier condensate of nonylphenol and ethylene oxide, for pastes and wettable powders); lubricating agents (for example liquid paraffin, talc, stearic acid, magnesium stearate or polyethylene glycol for tablets); dispersing agents (for example disodium salt of the condensation product of naphthalene sulphonic acid and formaldehyde, and calcium lignin sulphonate for wettable powders, pastes and suspensions); gelling agents (for example colloidal clays, sulphuric esters of a polysaccharide for aqueous suspension); suspending and thickening agents (for example gum tragacanth, xanthan gum, alginates, polyvinyl pyrrolidone, sodium carboxymethyl cellulose, and hydroxy-ethylcellulose for aqueous suspensions, aqueous-based pastes and wettable powders); and humectants (for example glycerine for water-based pastes); and other therapeutically acceptable accessory ingredients such as preservatives, buffers and antioxidants, which are known to be useful as carriers in such formulations.

A tablet may be prepared by compression or moulding, optionally with one or more accessory ingredients. Compressed tablets may be prepared by compressing in a suitable machine the active ingredient in a free flowing form such as a powder or granules, optionally mixed with a binder, lubricant, inert diluent, lubricating, surface active or dispersing agent. Moulded tablets may be made by moulding in a suitable machine, a mixture of the powdered compound moistened with an inert liquid diluent. Conveniently each tablet contains from 0.5 g. to 4.0 g of the active ingredient.

Granules may be made by the technique of wet granulation comprising moistening the powdered active ingredient with a binder in an inert liquid, and drying the moist mass; or by the techniques of precompression or slugging. The granules may be administered to animals in an inert liquid vehicle; or in a cachet or capsule of hard or soft gelatin preferably with liquid or powdered solid diluent; or in a suspension with a water or an oil base. In a drench or suspension, it is preferable to include further accessory ingredients such as a dispersing agent.

A dispersible or wettable powder may be made by admixing together the finely divided active ingredient with a wetting agent, and then administering the powder to the host animal as a suspension or dispersion in water. If desired a dispersing, suspending or thickening agent may be included. These formulations preferably contain from 15 to 85% by weight of the active ingredient.

A paste may be formulated in a liquid diluent which suspends the active ingredient. A stiffening or thickening agent may be included, together with a wetting agent and an humectant if the liquid diluent is water. If an emulsion paste is needed (oil-out or water-out), then one or more surface active agents should be included. From 25 to 80% by weight of these paste formulations may be comprised of the active ingredient but if the lower concentrations are used, then sufficient stiffening or thickening agent should be included to provide the desired viscosity.

Suspensions of the active ingredient in an inert liquid carrier are essentially the same as pastes but of a lower viscosity. They may be formulated using water or other inert diluent as the liquid carrier in association with a dispersing or wetting agent. Other ingredients such as thickening, gelling and suspending agents may also be included. These formulations may contain a wide range of concentrations of active ingredient, but of course, if too high a concentration is included the viscosity of the formulation will increase, and the formulations will become more of a paste than a suspension. Subject therefore to the concentration of the remaining ingredients, 5 to 50% by weight of the formulations may be comprised by the active ingredient.

In feed supplements, the active ingredient is generally present in large amounts relative to the accessory ingredients, and the supplements may be added directly or after intermediate blending or dilution. Examples of accessory ingredients for such formulations include solid orally ingestible carriers such as corn meal, attapulgite clay, soya flour, wheat shorts, soya grits, edible vegetable materials, and fermentation residues. The active ingredient is usually incorporated in one or more of the accessory ingredients and intimately and uniformly dispersed by grinding, tumbling or stirring with conventional apparatus. Formulations containing 1 to 90% by weight of the active ingredients are especially suitable for adding to feeds to provide a concentration desired to control infections by way of the animals' rations.

A compound of formula (I) may be administered either alone as the sole treatment for a liver fluke infection, or in combination with other substances which may complement or supplement its activity. Such additional substances may be administered simultaneously as a separate dose or in combination with a compound of formula (I) in a formulation, and may comprise other anthelmintics having activity against other parasites, such as cestodes (tapeworms) or nematodes. Such additional substances include phenothiazine; piperazine derivatives, for example the citrate, adipate or phosphate salts; organo-phosphorus compounds for example O,O-di-(2-chloroethyl)O-(3-chloro-4-methylcoumarin-7-yl)phosphate (Haloxon); 4-t-butyl-2-chlorophenyl N-methyl-O-methylphosphoramidate (Ruelene (Trade Name)); O,O-diethyl-O-(3-chloro-4-methyl-7-coumarinyl) phosphorothioate (Coumaphos); O,O-diethyl-O-naphthaloximide phosphate (Naphthalophos); O,O-dimethyl-2,2,2-trichloro-1-hydroxyethylphosphonate (Trichlorfon); benzimidazole anthelmintics including 2-(4-thiazolyl)benzimidazole (Thiabendazole); methyl 5-n-butybenzimidazole-2-carbamate (Parbendazole); and isopropyl-2-(4-thiazolyl)benzimidazole-5-carbamate (Cambendazole); quaternary ammonium anthelmintics including N-benzyl-N,N-dimethyl-N-(2-phenoxyethyl)ammonium salts such as the 3-hydroxy-2-naphthoate and embonate salts (Bephenium salts); N,N-dialkyl-4-alkoxy-$\alpha$-naphthamidine anthelmintics including N,N-dibutyl-4-hexyloxy-$\alpha$-naphthamidine (Bunamidine); salts of dl and 1-2,3,5,6-tetrahydro-6-phenylimidazo (2,1-b)thiazole (Tetramisole and Levamisole); trans-1-methyl-2-(2-(2-thienyl)vinyl)-1,4,5,6-tetrahydropyrimidine tartrate (Pyrantel tartrate); cis-1,4,5,6-tetrahydro-1-methyl-2-(2-(3-methyl-2-thienyl)vinyl)pyrimidine tartrate (Morantel tartrate); polyhalogenated benzanilide anthelmintics including 3,3',5,5',6-pentachloro-2,2'-dihydroxybenzanilide (Oxyclozanide); 2-acetoxy-4'-chloro-3,5-diiodobenzanilide (Clioxanide); 3,4',5-tribromosalicylanilide (Tribromsalan); 3,5-diiodo-3'-chloro-4'-(p-chlorophenoxy) salicylanilide (Rafoxanide); 4',5-dibromo-2-hydroxybenzanilide; 2,2'-dihydroxy-3,3'-dinitro-5,5'-dichlorobiphenyl (Menichlopholan); 2,2'-dihydroxy-3,3',5,5',6,6'-hexachlorodiphenylmethane (Hexachlorophene); 1,4-bis-(trichloromethyl)benzene (Hetol); 3-iodo-4-hydroxy-5-nitrobenzonitrile (Nitroxynil); and 5-chloro-N-(2'-chloro-4'-nitrophenyl)salicylamide (Niclosamide).

A particularly preferred combination comprises a compound of formula (I) and oxyclozanide, preferably in the ratio of 40 to 100 mg/kg and 2.5 to 15 mg/kg or lower respectively. Oxyclozanide is highly effective against adult liver flukes, and in combination with a compound of formula (I), complements its activity.

It will be appreciated that what we may claim may comprise any novel feature described herein but principally and not exclusively as follows:

(a) a compound of formula (I);
(b) a method of making such a compound of formula (I);
(c) a veterinary formulation comprising a compound of formula (I) together with a suitable carrier therefor;
(d) a method of making such a formulation and
(e) a method for the treatment of liver fluke infections in a mammal comprising the administration of a compound of formulation as described in paragraphs (a) or (b) above.

The following examples illustrate aspects of this invention but in no way are to be construed as a limitation thereof.

EXAMPLE 1

Preparation of 4-(4-propanamidophenoxy)phenyl methyl sulphone

4-[(4-Methylthio)phenoxy]aniline (10 g) dissolved in 100 ml of 95% ethanol was treated with 15 ml of propanoic acid anhydride with stirring at room temperature. Crystals formed immediately. After about 5 mins., the reaction was heated on steam, and water was added to incipient turbidity. On cooling, platelets formed. The reaction was stored at 4° C. overnight, then filtered. The product was obtained as off-white platelets. It was recrystallised from ethanol:water (approx. 70:30 by volume). A portion was dried for analysis at 100° C. (0.01 mm) overnight. Calculated for $C_{16}H_{17}NO_2S$: C, 66.87; H, 5.94; N, 4.88. Found: C, 66.59; H, 5.95; N, 4.67 (average of two analyses). The product 4-(4-methylthiophenoxy)-N-propanoylaniline, melted between 145.7° and 145.8° C.

4-(Methylthiophenoxy)-N-propanoylaniline (6.7 g; 0.0234 M) was placed in a 100 ml flask with propanoic acid (100 ml) at room temperature. It did not dissolve completely. 30% hydrogen peroxide (10 ml) was added at once with magnetic stirring. Further propanoic acid (100 ml) was added as washes. The solution became clear, and was stirred for 15 mins, and left to stand at room temperature overnight (approx. 25° C.). It was then heated on a water bath at 45° C.±5° C. for a day, and heated on the steam bath at internal temperature 95° C. for much of the night. At this time, a thin layer chromatogram (8:1 = benzene:acetone, silica gel) with detection by ultraviolet light, showed a single spot whose Rf was about 0.78. Water was added to the solution, which was heated on the steam bath to near turbidity. The solution was filtered with Filtrol 1, water was added to incipient turbidity, and the solution then cooled, finally to 4° C. After two weeks, platelets of melting point 152.4° to 154.4° C. were obtained. These were recrystallised for analysis from ethanol-water by dissolving in boiling 50% by volume ethanol(approx. 200 ml) and adding more water (an additional 300 ml) after filtration. The product was off-white platelets. It assumed a purplish colour after remaining in contact with the air. A sample was dried for analysis overnight at 100° C. (0.01 mm). Calculated for $C_{16}H_{17}NSO_4$, M.W. 319.38: C, 60.17; H, 5.37; N, 4.39. Found: C, 60.17; H, 5.38; N, 4.36. The melting point (air dried) of the product, 4-(4-propanamidophenoxy)phenyl methyl sulphone, was found to be 157.8° to 159° C.

EXAMPLE 2

Preparation of 4-(4-n-butanamidophenoxy)phenyl methyl sulphone

In accordance with the method described in Example 1 was prepared 4-(4-n-butanamidophenoxy)phenyl methyl sulphone, m.p. 134.3°–134.9° C.

EXAMPLE 3

Preparation of 4-(2-allyl-4-methylthiophenoxy)aniline

4-Allyloxyphenyl methyl·sulfide (157.3 g) in 1200 ml of N,N-dimethylaniline, and a few boiling chips, was heated under reflux under nitrogen, using a jacketted condenser. A stream of air was used for cooling. Refluxing was continued overnight. Thin layer chromatography indicated that only a small amount of starting material was left at this point, so the reaction was cooled under nitrogen, and added to a mixture of 1 liter of concentrated hydrochloric acid and 1 liter of cracked ice, with stirring. It was then extracted with benzene, and the benzene washed with two 250 ml portions of 1 N hydrochloric acid, and once with water. The benzene solutions were then extracted with 500 ml of 10% aqueous sodium hydroxide solution, then three times with 500 ml of 5% aqueous sodium hydroxide solution. All of the aqueous solutions were combined and acidified with hydrochloric acid. A little ice was added to keep the neutralization near room temperature. The resulting acidic solutions were extracted with ether, the ether dried over magnesium sulphate, and then the solutions were concentrated. The resulting oil was transferred to a round bottom flask and distilled, taking all that boiled between 176° C. (26 mm) and 192° C. (25 mm), mostly at 183.5°–187° C. (23 mm). Calculated for $C_{10}H_{12}OS$: C, 66.66; H, 6.71. Found: C, 66.55; H, 6.83. The product was 3-allyl-4-hydroxyphenyl methylsulphide.

3-Allyl-4-hydroxyphenyl methylsulphide (135.4 g) was dissolved in dried tertiary butanol (600 ml) under nitrogen, and potassium tert-butoxide [91 g (0.82 moles)] was added, followed by an additional 200 ml of tertiary butanol washes. The mixture was stirred, and formed a clear yellowish solution within 10 mins. p-Fluoronitrobenzene (118.3 g (0.84 mole)) was added in a thin stream over about 2 mins, at the initial reaction temperature of about 45° C., with constant vigorous stirring. The solution was stirred overnight, and was still alkaline, so it was heated on the steam bath under reflux for a total of two more days, and then cooled overnight. It was then decanted from the solids, and the decantate was evaporated down on steam bath at water pump pressure to leave an oil. The oil was partitioned between benzene and three 250 ml portions of 10% aqueous sodium hydroxide. (Acidification of each aqueous sodium hydroxide layer gave a little oil). The benzene which had been extracted with base was extracted once with approx. 300 ml of water, and dried briefly over magnesium sulphate. Distillation of the benzene left a residue. The initial solids similarly partitioned between water and benzene and the benzene extracted with N aqueous sodium hydroxide solution yielded more of a non-basic oil upon evaporation. The combined neutral oils were washed into a distillation flask with a little anhydrous ethanol, the solvents removed at the water pump, and the resulting oil distilled taking material boiling between 165° C. (95 microns) and 192°

C. (105 microns), mostly at the latter temperature. Oil was obtained at this point, which was redistilled in part, discarding a forerun boiling between 106° C. (35 microns) and 169° C. (38 microns). The flask residue solidified but could not be recrystallised. It was therefore again subjected to distillation, taking all material boiling between 182° C. and 194° C. (42 microns), mostly at 187° C.±1° (42 microns). Analysis: Calculated for $C_{16}H_{15}NO_3S$: C, 63.76; H, 5.02; N, 4.65. Found: C, 63.62; H, 5.08; N, 4.54. The product was 4-[2-allyl-4-(methylthio)phenoxy]nitrobenzene.

4-[2-Allyl-4-(methylthio)phenoxy]nitrobenzene (148 g (0.492 M) was reduced to the amino compound by placing it in a 3 liter 3 neck flask under nitrogen, and adding 14 ml of concentrated aqueous hydrochloric acid, 1400 ml of 95% ethanol and, while stirring, a total of 156 g (excess) of iron powder, a little at a time. The rate of addition of the iron was such as to allow the reaction, initially heated on a steam bath, to keep gently boiling. The total time of addition was approx. 8 mins. The reaction was then stirred and heated with steam for 2½ hrs, when a sample basified with sodium hydroxide and extracted with benzene, showed no starting material spot on thin layer chromatography. The reaction was allowed to remain standing overnight. The reaction mixture was next filtered, 50 ml of concentrated aqueous hydrochloric acid was added, and it was evaporated on the steam bath at water pump pressure until it solidified. The solid material was treated with approx. 500 ml of hot water, filtered hot, and washed with an additional 100 ml of hot water slightly acidified with hydrochloric acid to bring the oil produced by addition of water back into solution. The filtrate was treated with approx. 100 ml of concentrated aqueous hydrochloric acid. The solution precipitated an oil. This was dissolved by addition of approx. two more liters of water, heated, and finally made uniform by addition of approx. 100 ml of ethanol. The solution was cooled, adding more ethanol to redissolve the oil that came out, to near room temperature. Addition at room temperature of a little concentrated aqueous hydrochloric acid caused crystals to form. The solution was stored at 4° C. for 5 days, and the resulting mass of crystals was filtered off, washed with a little approx. 3 N aqueous hydrochloric acid, then a little ether. It was recrystallized from ethyl acetate-anhydrous ether, using about 1 liter of ethyl acetate and about 3 liters of ether added to incipient turbidity. It was then stored at 4° C. The resulting fine needles were filtered off, and dried at 64° C. (0.01 mm) for 4 hours for analysis. Calculated for $C_{16}H_{18}ClNOS$. ½ $H_2O$: C, 60.65; H, 6.04. Found: C, 60.42; H, 5.83 (average of two analyses). The m.p. (air dried) of the product 4-[2-allyl-4-methylthiophenoxy]aniline was 118°-120° C.

EXAMPLE 4

Preparation of 4-(4-acetamidophenoxy)-3-allylphenyl methyl sulphide

4-[2-Allyl-4-methylthiophenoxy]aniline hydrochloride (61 g) was dissolved in ethanol (95%, 350 ml) and acetic anhydride (12.5 ml) then N sodium hydroxide (200 ml) was added, with stirring. After subsequent addition of more acetic anhydride (12.5 ml) and more of N sodium hydroxide (50 ml), there was obtained after filtration, and recrystallisation from ethanol-water the acetamido compound; melting point 131.1°-131.9° C., 4-(4-acetamidophenoxy)-3-allylphenyl methyl sulphide.

EXAMPLE 5

Preparation of 4(4-acetamidophenoxy)phenyl methyl sulphoxide

A solution of 4-(4-methylthiophenoxy)acetanilide 2.46 g (0.00902 mole) in 100 ml of methanol was treated by stirring with 20 ml (0.01 mole) of an aqueous solution of 0.5 N sodium metaperiodate at room temperature. A voluminous precipitate formed, not dissolved by addition of 50 ml more of methanol. The resulting mixture, which had been vigorously swirled during the addition of periodate, was stored at 4° C. overnight. Thin layer chromatography on silica gel using a 1:1 mixture of benzene-ether showed starting material and another spot, so the reaction was kept for another 9 days. It was then treated with an equal volume of methanol, filtered and the filtrate evaporated on the steam bath at water pump pressure. The resulting small amount of "grease" was boiled up with approx. 700 ml of 95% ethanol, in several portions, filtering the supernatant liquid from a small amount of water-soluble residue, at the boiling point. Dilution to about 1900 ml with water, and storage at 4° C. for 18 days gave white crystalline material, m.p. 159.2°-161.2° C. It was recrystallised for analysis from ethanol-water, using about 80 ml of 95% ethanol and adding water to incipient turbidity near the boiling point. Ten days storage at 4° C. led to crystallisation of a white solid. Analysis: Calculated for $C_{15}H_{15}NSO_3$, molecular 289.35: C, 62.26; H, 5.23; N, 4.84. Found: C, 61.97; H, 5.22; N, 4.71. m.p. 162.1°-162.4° C. The product was 4-(4-acetamidophenoxy)phenyl methyl sulphoxide.

EXAMPLE 6

Preparation of 4-[4-acetamidophenoxy]-3-chlorophenyl methyl sulphone

2-Chloro-4-(methylthio)phenol 14.25 g and 200 ml of dried tertiary butanol were placed in a 3-neck round bottom flask with stirrer, condenser and addition funnel. 11.3 g of potassium tert-butoxide was added under nitrogen. After about 10 mins of stirring, 16.5 g of p-fluoronitrobenzene was added all at once, and the reaction mixture was stirred vigorously for a few minutes, then heated on the steam bath for 2 days. It was still alkaline, so an additional 5 g of p-fluoronitrobenzene was added, and stirring and heating were continued for another day. After this time the pH of a sample removed from the reaction was pH 8 (wet indicator paper) so the reaction mixture was evaporated on the steam bath at the water pump, partitioned between water and ether, and the ether was extracted with two 100 ml portions of N/2 aqueous sodium hydroxide and dried over magnesium sulphate overnight. Acidification of the aqueous alkaline extracts yielded small amounts of an oil, indicating that the reaction had not yet been completed.

Evaporation of the ether left an oil which was transferred with anhydrous ether through a filter paper into a round bottom flask. It was fractionally distilled, collecting a yellow oil boiling between 171° C. (97 microns) and 182° C. (97 microns). This product, 3-chloro-4-(4-nitrophenoxy)phenyl methyl sulphide was used without further purification.

In a round bottom 3-neck flask with an efficient stirrer and a reflux condenser was put 3-chloro-4-(4-nitrophenoxy) phenyl methyl sulphide 20.8 g (0.0705 M if pure), 25 g (excess) of iron powder, 250 ml of 95% ethanol, and 1 ml of concentrated aqueous hydrochloric acid. The mixture was stirred and heated on a steam bath overnight. The next day, 20 ml of acetic anhydride was added to the hot solution in a thin steam with stirring, and the hot solution was then filtered. The filtrate was evaporated at water pump pressure on the steam bath to about half its volume. The resulting tan crystals were dissolved by heating the mixture on steam to the boiling point, and treated with an equal volume of water. The solution turned darker, and was treated with decolourising charcoal and Filtrol 19 and heated and filtered, adding more ethanol to keep the crystals in solution during the rather slow filtration. After having been cooled for about 3 hours, nearly white needles of m.p. 143°–147° C. were obtained. These were recrystallised for analysis from ethanol-water, giving nearly white felted needles. A portion dried for analysis at 78° C. (0.01 mm) for 5 hours gave: Calculated for $C_{15}H_{14}ClNO_2$ S,M. W. 307.80: C, 58.53; H, 4.58; N, 4.55. Found: C, 58.23; H, 4.69; N, 4.80. The product, 4-(4-acetamidophenoxy)-3-chlorophenyl methyl sulphide had a m.p. of between 146.8° and 147.2° C.

A solution of 14.7 g (0.0478 M) of 4-(4-acetamidophenoxy)-3-chlorophenyl methyl sulphide in 500 ml of glacial acetic acid was treated with 17 g of nominally 30% aqueous hydrogen peroxide. After having been swirled, the mixture was allowed to remain at a temperature of 60°±10° C. overnight, and then heated for 3 days at steam bath temperature. At this time there was a faint positive test for peroxide, so the solution was treated with a small amount of 5% palladium on charcoal catalyst, stirred, and filtered after a few minutes. Evaporation on the steam bath at water pump pressure of the solvents left a dark tan oil, which crystallised on being boiled briefly with absolute ethanol. It was recrystallised from ethanol-water. Analysis: Calculated for $C_{15}H_{14}ClNO_4S$,M.W. 339.80: C, 53.02; H, 4.15; N, 4.12. Found: C, 52.89; H, 4.19; N, 4.09. The melting point varied somewhat with the rate of heating, but was in the range of from 187.8°–188.7° for material equilibrated with air. The product was, 4-(4-acetamidophenoxy)-3-chlorophenyl methyl sulphone.

EXAMPLE 7

Preparation of 4-(4-aminophenoxy)-3-methylphenyl methyl sulphide

A. Preparation of 4-(4-nitrophenoxy)-3-methylphenyl methyl sulphide

A solution of 126.4 g (0.822 mole) of 4-thiomethyl-m-cresol in approx. 900 ml of dry tertiary butanol was treated at about 50° C. under nitrogen with 99.5 g (0.88 mole) of potassium tert-butoxide. The mixture was stirred under nitrogen for a few minutes, and 139.5 g of p-fluoronitrobenzene was dropped in with stirring over about two minutes. The reaction was stirred, then stirring was stopped and it was allowed to remain for ½ hour, then warmed and kept at 50°–60° C. for five days. It was then heated under reflux for an additional day, filtered hot, and a little water was added to the filtrate. The product boiled out, so 95% ethanol was added to bring it back into solution. The solution was seeded with a little material obtained by scratching in the test tube, and then crystallised nicely on cooling. It was stored at 4° C. for 8 days. The product was filtered off, m.p. 81.6°–84.4° C. Recrystallisation from approx. 800 ml of 95% ethanol and 1600 ml of absolute ethanol yielded yellow platelets. A sample was dried for analysis at 61° C. (0.01 mm) for 4 hours, and melted 84°–85.4°

C. Analysis Calculated for $C_{14}H_{13}NO_3S$: C, 61.07; H, 4.76; N, 5.09. Found: C, 60.96; H, 4.66; N, 4.95.

B. Preparation of 4-(4-Aminophenoxy)-3-methylphenyl methyl sulphide 4-(4-Nitrophenoxy)-3-methylphenyl methyl sulphide (120 g, 0.437 M) in 1.5 L of 95% ethanol was placed in a 3 L round bottom flask equipped with a stirrer, a reflux condenser, and a nitrogen inlet and a dropping funnel. After 6 ml of concentrated aqueous HCl had been added, 295 g of iron powder (excess, electrolytic iron, Matheson & Co.) was added over approximately 10 min in a slow stream at initial temperature 45° C. Stirring was continued for 1.5 hrs and then the reaction mixture was heated on steam under reflux and an additional 300 g of iron powder was added and stirring continued for 2 hr. more. The resulting suspension of iron and iron oxides was filtered with a filter aid [Supercel (Trade Mark)]. The clear filtrate and washes tended to darken in air moderately quickly. They were refiltered to remove the ferric hydroxide formed in contact with air, and immediately evaporated down on the steam bath at water pump pressure. The residue of this condensation was 82.2 g of a dark, rust-coloured liquid. This was dissolved in a total of 500 ml of water containing slightly over the theoretical amount of hydrochloric acid, and refiltered hot in the presence of more filter aid. The filter aid was washed with 200 ml more of hot water, and the whole aqueous filtrate was treated with concentrated hydrochloric acid until no more crystals appeared to come out, heated to near the boiling point, and cooled to approximately 40° C. The resulting white to salmon coloured solid was then filtered off. This melted at 162° C. and weighed 98 g. It was recrystallized from approximately 750 ml of hot water, adding a little aqueous hydrochloric acid to the washes and filtrates to retain the base in solution, then adding approximately 100 ml of concentrated hydrochloric acid and approximately 50 ml of water to the hot solution. It was cooled, and filtered at room temperature after about 1 hr. The product melted at 155°–158°, mostly at 157.5° C. Analysis: For $C_{14}H_{16}ClNOS$, M.W. 281.81: C, 59.66; H, 5.72; N, 4.97. Found: C, 59.52; H, 5.81; N, 4.82.

EXAMPLE 8

Preparation of 4-(4-acetamidophenoxy)-3-methylphenyl methyl sulphide

4-Nitrophenyl 3-methyl-4-methylthio phenyl ether (120 gms (0.437 mole)) prepared according to Example 7A, dissolved in 1.5 liters of 95% ethanol in a mechanically stirred 3l flask, was heated initially to approximately 45° C., and iron powder, 295 gm, was added with stirring during about 10 minutes in a slow stream. The reduction was maintained at 45° C. to 55° C., and stirring was continued for 1½ hours. An additional 300 gms of finely divided iron was added all at once at that point, and the reaction mixture was stirred for 3.2 additional hours, using steam heat to maintain the temperature. The resulting mixture was filtered in the presence of supercel. The clear filtrate and washings were refiltered into a round bottomed flask and solvent was removed by evaporation at the water pump. The residue was a dark, rusty looking liquid. This was dissolved in 500 ml of water holding slightly over the theoretical amount of hydrochloric acid, and filtered hot using a filter aid, the filtrate washed with approx. 200 ml more of hot water, and concentrated aqueous hydrochloric acid was added until crystals barely formed at about the boiling point. Cooling led to crystallisation of the product; 4-(4'-thiomethyl-3'-methyl) phenoxy aniline hydrochloride, m.p. 162° C. This was recrystallised from about 750 ml of hot water, adding a little Normal hydrochloride to the washes to prevent precipitation, presumably of the base. The filtrate was treated with 100 ml of concentrated hydrochloric acid diluted with about 50 ml of water initially at approx. 40° C. and cooled under the tap. It was then filtered at about 30° C., to yield a crystalline solid.

This solid was dissolved in ethanol and treated with first excess of acetic anhydride, and then, with stirring, with dilute aqueous sodium hydroxide solution until strongly alkaline. After about 10 minutes, the reaction was treated with water to faint turbidity and left to stand. Platelets of the product 4-(4-acetamidophenoxy)-2-methylphenyl methyl sulphide, come out of solution slowly, melting point 99.6° to 101° C. On recrystallisation from ethanol-water, analytical samples were obtained melting between 101.4° and 102.1° C.

EXAMPLE 9

Preparation of 4-(4-acetamidophenoxy)-3-methylphenyl methyl sulphone.

In accordance with the method described in Example 8, there was prepared 4-(4-acetamidophenoxy)-3-methylphenyl methyl sulphone, m.p. 168.6°–169.3° C.

EXAMPLE 10

Preparation of 4-(4-acetamidophenoxy)benzyl ethyl sulphone p-Cresol (190 g; 1.76 mol), potassium-tert-butoxide (220.2 g; 1.93 mol) and t-butanol (from calcium hydride; 1 l) were stirred at room temperature, under nitrogen, for 15 mins; followed by the dropwise addition of p-fluoronitrobenzene (272.7 g; 1.93 mol). After heating at reflux for 18 hours, followed by cooling, the resulting yellow precipitate was removed by filtration and washed with absolute ethanol. The combined filtrate and washings were evaporated on the Buchi and the residue taken up in benzene (4 l). The combined benzene layers were dried over magnesium sulphate and evaporated to yield a yellow residue which was recrystallised from hexane (2 l) to give 4-(4-nitrophenoxy)toluene as a yellow solid. m.p. 65°–66° C. NMR (CDCl$_3$): 8.01 (d, 2H), 7.5 (q, 6H) and 2.31 (s, 3H). Analysis for $C_{13}H_{11}NO_3$: Calculated: C, 68.10, H, 4.84, N, 6.11; found: C, 68.13; H, 4.87; N, 6.14.

To a refluxing (250 watt infra-red lamp) and stirred solution of 4-(4-nitrophenoxy)toluene (229.25 g; 1 mol) in CCl$_4$ (2.5 l) under nitrogen, bromine (247.46 g; 1.55 mol) in CCl$_4$ (250 ml) was added dropwise over a period of 4 hours. After refluxing an additional 8 hours, followed by stirring at room temperature overnight, the reaction mixture was washed with 10% sodium bisulphite (1×1 l), saturated sodium bicarbonate (2×2 l) and saturated sodium chloride. The organic layer was dried over magnesium sulphate and evaporated to give a yellow solid which was recrystallised from benzene-hexane (250 ml:350 ml) to yield 4-(4-nitrophenoxy)α-bromotoluene as light yellow crystals. m.p. 68°–70° C. NMR (CDCl$_3$): 8.15 (d,2H), 7.45 (d,2H), 7.0 (d,4H); and 4.49 (s,2H). Analysis: calculated for $C_{13}H_{10}BrNO_3$: C, 50.67; H, 3.27; N, 4.55; Br, 25.93; found: C, 50.38; H, 3.24; N, 4.58; Br, 26.02.

To a solution of 4-(4-nitrophenoxy)-α-bromotoluene (70.0 g; 0.227 mol) in t-butanol (from calcium hydride, 500 ml), stirred under nitrogen, was added dropwise over a period of 15 mins a solution of potassium thioethylate (0.25 mol, previously prepared from potassium t-butoxide (28.01 g; 0.25 mol) and ethan thiol (15.52 g; 0.25 mol) in t-butyl alcohol (250 ml) and transferred to an addition funnel under nitrogen) in t-butanol. After stirring for 18 hours at room temperature, the reaction mixture was evaporated to give a semi-solid residue which was dissolved in 1:1 ether-benzene (1.5 l), washed with water (3×300 ml), dried over magnesium sulphate and concentrated to give an oil identified as 4-(4-nitrophenoxy)benzyl ethyl sulphide by its NMR spectrum (CDCl$_3$): 8.10 (m,2H), 6.9–7.6 (br m, 6H), 3.75 (s,2H), 2.48 (q,2H) and 1.25 (t,3H).

Crude 4-(4-nitrophenoxy)benzyl ethyl sulphide (51.0 g; 0.176 mol) was dissolved in acetic acid (500 ml) and a solution of hydrogen peroxide (25%, 71.95 g; 0.529 mol) in acetic acid (200 ml) was added dropwise over a 1 hr. period so that the temperature did not rise above 35° C. The mixture was then cautiously heated to 100° C. for a period of 18 hours at which time the solution gave a negative starch-iodide test. The mixture was cooled and the product precipitated by pouring on to an ice-water slush (1 l) containing sodium sulphite (20 g). The mixture was extracted with three portions of ether (1 l), 500 ml, 500 ml) and the etheral extracts were washed with water (4×300 ml), dried over magnesium sulphate and concentrated to provide 4-(4-nitrophenoxy)benzyl ethyl sulphone as an oil (containing ca. 15% acetic acid by NMR ($\delta$ 4.50,s, benzyl CH$_2$—) which was directly hydrogenated in ethanol (150 ml) over platinum (IV) dioxide at between 40 to 50 psi until a total of 0.387 mol of hydrogen had been absorbed. This required about 48 hours, during which time seveal additional quantities of catalyst were added. The mixture was filtered through Celite and evaporated. The residue was dissolved in ether-benzene (1:1 500 ml) and washed with 1 N sodium hydroxide (100 ml), dried over magnesium sulphate and filtered. Acetic anhydride (40 ml) was added, and the mixture was concentrated at 40° C. with a rotary evaporator to yield a pale brown solid. Recrystallisation from ethanol provided the acetylated product 4-(4-acetamidophenoxy)benzyl ethyl sulphone as pale brown flakes: m.p. 185.5°–186° C., NMR (DMSO-d$_6$): 9.91 (s,1H), 7.7–6.87 (br m, 8), 4.45 (s, 2H), 3.05 (q,2H), 2.22 (t,3H) and 2.05 (s,3H). Analysis calculated for $C_{17}H_{19}NO_4S$: C, 61.22; H, 5.74; N, 4.20; found: C, 61.26; H, 5.82; N, 4.23.

EXAMPLE 11

Preparation of 4-(4-acetamidophemoxy)benzyl methyl sulphone

In accordance with the method described in Example 10 there was prepared 4-(4-acetamidophenoxy)benzyl methyl sulphone, m.p. 201°–202° C.

EXAMPLE 12

Preparation of 4-(4-acetamidophenoxy)phenyl methyl sulphoxide 4-acetamidophenoxyphenyl methyl sulphide, 2.46 g (0.02 M) was dissolved in 100 ml of warm methanol and cooled to 24° C. Twenty ml of 0.5 M potassium periodate in aqueous solution at room temperature was added with stirring followed by 50 ml more of methanol. A precipitate formed immediately. The reaction was stored at 4° C. in a refrigerator for 9 days. A white, largely inorganic, solid was then removed by filtration and washed with methanol. The combined filtrates were evaporated in vacuo at water pump pressure while the flask was heated with hot water at a maximum temperature of 40° C. A thin layer chromatogram showed some starting material, none of the sulphone, and another product. The resulting oil was dissolved in 900 ml of boiling ethanol, filtered and diluted with water to approximately 1.9 L total volume, then stored at 4° C. After 4 weeks platelets were obtained. These had m.p. 159.2°–161.2° C., and after recrystallization for analysis from ethanol-water melted 162.1°–162.4° C.

EXAMPLE 13

4-(4-Acetamidophenoxy)phenyl methyl sulphone 5.46 g (0.02 M) of 4-(4-acetamidophenoxy)phenyl methyl sulphide was dissolved in 100 ml of methanol at about 50° C., and 300 ml more of methanol was added. The solution was cooled at 2° C., and 100 ml of 0.5 M potassium periodate solution was added, it being at room temperature. The internal temperature went up to 20° C. and much solid precipitated. More potassium periodate was added after a short time until a total of 460 ml of potassium periodate solution had been added. An additional 100 ml of methanol was added to restore some solubility to the organic material, and the combination was stored for 1 week at 4° C. A thin layer chromatogram using silica gel and equal volumes of benzene and acetone showed starting material present, the product, and another spot presumably of sulphoxide. Evaporation of solvents until crystals started forming, using a water bath not heated over 40° C. and water pump vacuum, followed by dilution of the resulting aqueous material with water and stored at 4° C. gave a solid melting 142.7° to 143.5° C., whose melting point was depressed by admixture with starting material. 5 g of solid so produced and recrystallized for analysis from 95% ethanol, by dilution with about a 5-fold excess of water near the boiling point, to incipient tubidity to yield 4-(acetamidophenoxy)phenyl methyl sulphone as white crystals melting 142.5° to 143.4° C.

EXAMPLE 14

Preparation of 4-[4-(Methylthio)phenoxy]aniline hydrochloride

4-Thiomethyl-4-nitro-phenyl ether (10 g; 0.038 mole), 95% ethanol (150 ml), and iron powder (25.5 g) were stirred under nitrogen while concentrated hydrochloric acid (3.0 ml) was added dropwise. The mixture was heated at reflux on the steam bath for 3 hours with continuous stirring. The resulting mixture was cooled and filtered through filtering aid (Filtroal (trade mark) 19). The alcohol solution was dried over sodium sulphate which was removed by filtration, and the ethanol filtrate evaporated on the steam bath at water pump pressure to leave a dark red oil (8.6 g). This was treated with 500 ml of saturated ethereal hydrogen chloride. A white-grey solid precipitated and was removed by filtration and washed with ether then recrystallized from anhydrous ethanol-anhydrous ether to yield 4-[4-(methylthio)phenoxy] aniline hydrochloride (5.5 g), melting point 200°–203° C.

EXAMPLE 15

| Aqueous Suspensions | | | | |
|---|---|---|---|---|
| Compound of Ex. 6 | 5.0% | 20.00% | 40.00% | 50.00% w/w |
| Bentonite (Gelling Agent) | 2.5% | 1.50% | 1.00% | 1.00% w/w |
| Bevaloid Dispersant (Trade Mark) Dispersing agent | 1.0% | 1.00% | 1.00% | 1.00% w/w |
| Sodium Benzoate (Buffering agent) | 1.0% | 1.00% | 1.00% | 1.00% w/w |
| Water | 90.5% | 76.50% | 57.00% | 47.00% w/w |
| | 100.0% | 100.00% | 100.00% | 100.00% w/w |

The bentonite was dispersed in some of the water, the Bevaloid Dispersant and sodium benzoate added, and finally the finely ground active ingredient with the water. The whole was mixed until uniform.

Bentonite is a colloidal clay consisting principally of montmorilonite and Bevaloid Dispersant is a disodium salt of the condensation product of naphthalene sulphonic acid and formaldehyde.

EXAMPLE 16

| Aqueous Suspensions | | | |
|---|---|---|---|
| Compound of Ex. 6 | 30.00% w/w | 20.00% w/w | 50.00% w/w |
| Sulphite Residue (Dispersing agent) | 5.00% w/w | 5.00% | 5.00% w/w |
| Carmoss (Gelling agent) (Trade Mark) | 0.75% w/w | 0.75% w/w | 0.75% w/w |
| Water | 64.25% w/w | 74.25% w/w | 44.25% w/w |
| | 100.00 w/w | 100.00% w/w | 100.00% w/w |

The Carmoss and sulphite residue were dissolved in the water, the finely ground active ingredient added, and the whole mixed until uniform.

Sulphite residue is crude calcium lignin sulphonate; Carmoss is a carragenate or a sulphuric acid ester of a polysaccharide.

EXAMPLE 17

| Aqueous Suspension | |
|---|---|
| Compound of Example 11 | 5.0% w/w |
| Neosyl (Trade Mark) (Diluent) | 5.0% w/w |
| Carmoss (Gelling agent) (Trade Mark) | 1.5% w/w |
| Bevaloid Dispersant (Trade Mark) (Dispersing agent) | 1.0% w/w |
| Water | 87.5% w/w |
| | 100.0% w/w |

The Carmoss and Bevaloid Dispersant were mixed with the water, and then the finely ground active ingredient was then added and the whole mixed until uniform. Where China clay was an ingredient, it was included at the same time as the addition of Bentone 38 is a cationic substituted with a quaternary ammonium base.

EXAMPLE 18

| Water-based Pastes | | | | |
|---|---|---|---|---|
| Compound of Ex. 11 | 23.0% | 55.00% | 60.00% | 45.00% w/w |
| Keltrol (Trade Mark) (Suspending agent) | 0.5% | 0.50% | 0.45% | 0.55% w/w |

Water-based Pastes (continued)

| | | | | | |
|---|---|---|---|---|---|
| Neosyl (Trade Mark) (Diluent) | 18.3% | — | 5.00% | — | w/w |
| Glycerine (Humectant) | 23.0% | 20.00% | 18.00% | 32.00% | w/w |
| Water | 35.2% | 24.50% | 16.55% | 32.45% | w/w |
| | 100.0% | 100.00% | 100.00% | 100.00% | w/w |

The Keltrol was dissolved in the water, the remaining ingredients incorporated, and the whole mixed until uniform.

Keltrol is a xanthan gum, a high molecular weight linear polysaccharide.

EXAMPLE 19

| Water-based Pastes | | | | | |
|---|---|---|---|---|---|
| Compound of Ex. 11 | 20.0% | 50.00% | 60.00% | 40.00% | w/w |
| Bevaloid Dispersant (Trade Mark) (Dispersing agent) | 0.5% | 0.50% | 0.40% | 0.60% | w/w |
| Gum tragacanth (Suspending agent) | 3.5% | 2.00% | 1.60% | 2.40% | w/w |
| Glycerine (Humectant) | 16.0% | 8.50% | 8.00% | 11.00% | w/w |
| Water | 60.0% | 39.00% | 30.00% | 46.00% | w/w |
| | 100.0% | 100.00% | 100.00% | 100.00% | w/w |

The gum tragacanth was dissolved in the mixture of water and glycerine, and the finely divided active ingredient incorporated to provide a uniform paste.

EXAMPLE 20

| Pastes | | | | | |
|---|---|---|---|---|---|
| Compound of Ex. 10 | 50.0% | 60.0% | 50.0% | 60.0% | 20.0% w/w |
| Polyethylene Glycol 400 | 40.0% | 32.0% | 50.0% | 40.0% | 45.0% w/w |
| Polyethylene Glycol 4000 | 10.0% | 8.0% | — | — | 5.0% w/w |
| China clay (Solid diluent) | — | — | — | — | 30.0% w/w |
| | 100.0% | 100.0% | 100.0% | 100.0% | 100.0% w/w |

Both glycols, or the single glycol, as appropriate, were heated together, and when uniform, the finely ground active ingredient (together with the china clay, if appropriate) was added, and the mixture stirred to provide a paste of uniform consistency.

EXAMPLE 21

| Pastes | | | | |
|---|---|---|---|---|
| Compound of Ex. 10 | 50.0% | 60.0% | 40.0% | 20.0% w/w |
| Carmoss (Trade Mark) (Thickening agent) | 2.0% | 1.6% | 2.5% | 1.7% w/w |
| Glycerine (Humectant) | 10.0% | 8.0% | 12.0% | 8.3% w/w |
| Water | 38.0% | 30.4% | 45.4% | 31.7% w/w |
| China Clay (Solid Diluent) | — | — | — | 38.3% w/w |
| | 100.0% | 100.0% | 100.0 | 100.0% w/w |

The Carmoss was dissolved in the water, the glycerine added, followed by the active ingredient (and China Clay, if appropriate). The whole was mixed until uniform.

Carmoss is a carragenate or a sulphuric acid ester of a polysaccharide.

EXAMPLE 22

| Pastes | | | | |
|---|---|---|---|---|
| Compound of Ex. 10 | 60.0% | 70.00% | 45.0% | 20.0% |
| Manucol (Trade Mark) (Thickening agent) | 0.3% | 0.25% | 0.4% | 1.5% w/w |
| Glycerine (Humectant) | 8.0% | 6.00% | 11.0% | 5.0% w/w |
| Water | 31.7% | 23.75% | 43.6% | 38.5% w/w |
| China Clay (Solid Diluent) | — | — | — | — |
| | 100.0% | 100.00% | 100.0% | 100.0% w/w |

The Manucol was dissolved in the water and glycerine and the active ingredient (and China Clay, if appropriate) added and mixed until uniform.

Manucol is sodium alginate.

EXAMPLE 23

| Oil-in-Water Emulsion Pastes | | |
|---|---|---|
| Compound of Ex. 1 | 5.00% w/w | 50.0% w/w |
| Sipol Wax AO (Trade Mark) (Emulsifying agent) | 6.25% w/w | 5.0% w/w |
| Mineral Oil (Liquid Diluent) | 25.00% w/w | 20.0% w/w |
| Water | 31.35% w/w | 25.0% w/w |
| China Clay (Solid Diluent) | 17.50% w/w | — |
| | 100.00% w/w | 100.0% w/w |

The Sipol wax AO was dissolved in the mineral oil at 60° C., and this solution then added with vigorous stirring to the water, also at 60° C. Stirring was continued unitl the emulsion was cooled to 25°–30° C., at which temperature the finely ground active ingredient (and the China Clay where appropriate) was added, and the whole mixed until uniform.

Sipol wax AO is Cetomacrogol Emulsifying Wax BPC.

EXAMPLE 24

| Wettable Powders | | |
|---|---|---|
| Compound of Ex. 1 | 85.0% w/w | 20.0% w/w |
| Neosyl (Trade Mark) (Diluent) | 1.0% w/w | 24.0% w/w |
| Bevaloid Dispersant (Trade Mark) (Dispersing agent) | 2.0% w/w | 2.0% w/w |
| Perminal BX (Trade Mark) (Wetting agent) | 0.2% w/w | 0.2% w/w |
| Natrosol 250 (Trade Mark) (Suspending agent) | 1.7% w/w | 2.8% w/w |
| Sodium sulphate (Suspending agent) | 10.1% w/w | 51.0% w/w |
| | 100.0% w/w | 100.0% w/w |

The raw materials were mixed together to provide a powder of uniform consistency. Perminal BX is the sodium salt of alkylated naphthalene sulphonic acid.

EXAMPLE 25

| Feed Premixes | | |
|---|---|---|
| Compound of Ex. 1 | 1% w/w | 80% w/w |
| Cereal Base | 99% w/w | 20% w/w |

The two materials were mixed to provide a premix of uniform consistency.

EXAMPLE 26

| Pellets | | |
|---|---|---|
| Compound of Ex. 13 | 1% w/w | 80% w/w |
| Cereal Base | 99% w/w | 20% w/w |

The two ingredients were mixed, and the mixture then fed to any conventional feedstuff pelleting plant.

EXAMPLE 27

Tablets
Tablets were prepared from the following ingredients:-

| | per tablet |
|---|---|
| Compound of Ex. 13 | 2000 mg |
| Starch B.P. | 300 mg |
| Povidone B.P.C. | 50 mg |
| Magnesium stearate B.P. | 25 mg |

Item 2 and half the quantity of starch were granulated with a solution of povidone in 50% aqueous ethanol, and dried. The remainder of starch, and Magnesium stearate were added and the whole mixed. The resulting granules were then compressed with a suitably shaped punch.

EXAMPLE 28

Tablets
Tablets were prepared from the following ingredients:-

| | per tablet |
|---|---|
| Compound of Ex. 13 | 2000 mg |
| Microcrystalline cellulose | 1000 mg |
| Methylhydroxyethylcellulose | 50 mg |
| Starch B.P. | 250 mg |
| Magnesium stearate. | 30 mg |

Item 1, together with half the quantity of items 2 and 4, were granulated with a solution of item 3 in 50% aqueous ethanol, and then dried. The remainder of items 2 and 4 were added, and then item 5, and the whole mixed together. The resulting granules were dried and then compressed to form tablets.

EXAMPLE 29

Groups of five mice were each injected at day zero with 12 *Fasciola gigantica* metacercariae.

The mice in each group were orally dosed with a compound of formula (I) once on days 6 to 10 inclusive. At day 31 the mice were autopsied to ascertain the number of living metacercariae in the liver.

The percentage inhibition of the treated groups of mice was termined for each compound tested by comparison with undosed controlled groups similarly infected at day zero with 12 *F. gigantica* metacercariae and autopsied at day 31.

The results are illustrated in Table 1 where the following score has been used to indicate percentage inhibition.

| SCORE | INHIBITION |
|---|---|
| ++++ | (91-100)% |
| +++ | (75-90)% |
| ++ | (51.74)% |

Percentage inhibition =
$$\frac{\text{Number of living metacercariae in treated group}}{\text{number of living metacerariae in control group}} \times 100\%$$

TABLE 1

% inhibition of *F. gigantica* metacerariae in mice treated with certain compounds of formula (1)

| COMPOUND | DOSE mg/kg orally | SCORE |
|---|---|---|
| 4-(4-Acetamidophenoxy)-3-methylphenyl-methyl sulphide | 200 | ++++ |
| 4-(4-Acetamidophenoxy)phenylmethyl sulphoxide | 200 | ++++ |
| 4-(4-Acetamidophenoxy)benzylethyl sulphone | 200 | ++++ |
| 4-(4-Acetamidophenoxy)benzyl-methyl sulphone | 200 | ++++ |
| 4-(4-n-butanamidophenoxy)phenyl-methyl sulphone | 200 | ++++ |
| 4-(4-n-propanamidophenoxy)phenylmethyl sulphone | 200 | ++++ |
| 4-(4-Acetamidophenoxy)phenylmethyl sulphone | 200 | ++++ |
| 4-(4-Acetamidophenoxy)-3-methylphenyl-methyl sulphone | 200 | ++++ |
| 4-(4-Acetamidophenoxy)-3-chloro-phenylmethyl sulphone | 200 | ++++ |

What we claim is:
1. A diphenylether of the formula

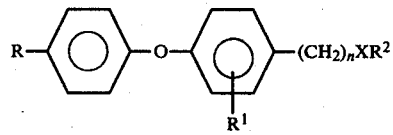

or an acid addition salt thereof wherein
R is selected from monoalkanoylamino and dialkanoylamino, both of one to four carbon atoms;
$R^1$ is selected from hydrogen, alkyl of one to four carbon atoms, alkenyl of two to five carbon atoms and halo;
$R^2$ is alkyl of one to four carbon atoms;
X is S or $SO_2$: and
n is 0, 1, 2 or 3.
2. A diphenylether as claimed in claim 1 wherein
R is monoalkanoylamino of two or three carbon atoms;
$R^1$ is hydrogen;
$R^2$ is alkyl or one or two carbon atoms;
X is $SO_2$; and
n is 0 or 1
3. A diphenylether selected from the class consisting of:
4-(4-acetamidophenoxy)phenyl methyl sulphone,
4-(4-propanamidophenoxy)phenyl methyl sulphone,
4-(4-acetamidophenoxy)benzyl methyl sulphone, and
4-(4-acetamidophenoxy)benzyl ethyl sulphone.
4. A veterinary formulation for the treatment of liver fluke infection which comprises a diphenylether as defined in any of claims 1 to 3, in an anti-fluke infection effective amount, in association with a veterinarily acceptable carrier therefor.

5. A formulation as claimed in claim 4 suitable for oral administration.

6. A formulation as claimed in claim 5 as a discrete unit dose.

7. A formulation as claimed in claim 4 wherein the carrier is a solid.

8. A formulation as claimed in claim 6 as a tablet, bolus, capsule, cachet or electurary.

9. A formulation as claimed in claim 8 which contains 0.5 to 4 g of a diphenylether as defined in any of claims 1 to 3.

10. A method for the treatment of liver fluke infections in a mammal comprising the administration to said mammal of an anti-fluke infection effective amount of a diphenylether as defined in any of claims 1 to 3.

11. The compound of claim 1 in which n is 0.

12. The compound of claim 1 in which X is S.

* * * * *